United States Patent
Rajamani et al.

(10) Patent No.: US 9,010,198 B2
(45) Date of Patent: Apr. 21, 2015

(54) AIRCRAFT DEBRIS MONITORING SENSOR ASSEMBLY

(75) Inventors: Ravi Rajamani, West Hartford, CT (US); Alexander I. Khibnik, Glastonbury, CT (US); William Donat, Manchester, CT (US); Rajendra K. Agrawal, S. Windsor, CT (US)

(73) Assignee: United Technologies Corporation, Hartford, CT (US)

( * ) Notice: Subject to any disclaimer, the term of this patent is extended or adjusted under 35 U.S.C. 154(b) by 459 days.

(21) Appl. No.: 13/194,096

(22) Filed: Jul. 29, 2011

(65) Prior Publication Data

US 2013/0025348 A1   Jan. 31, 2013

(51) Int. Cl.
| | |
|---|---|
| G01F 13/00 | (2006.01) |
| G01N 15/02 | (2006.01) |
| G01P 5/165 | (2006.01) |
| G01N 15/06 | (2006.01) |

(52) U.S. Cl.
CPC ............ *G01N 15/0266* (2013.01); *G01P 5/165* (2013.01); *G01N 15/0272* (2013.01); *G01N 15/0656* (2013.01)

(58) Field of Classification Search
CPC ........... B64F 1/005; G01P 5/165; F04D 1/12; B04B 11/02; B08B 15/023; A61K 2300/00; A61K 39/00; A61B 5/14532; A61B 5/1411; A61B 17/1764; A61B 19/04; A61B 19/08; A61B 19/2203; G01N 21/94
USPC ................ 73/65, 583, 592, 855, 861, 861.41, 73/23.33, 28.01, 865.5
See application file for complete search history.

(56) References Cited

U.S. PATENT DOCUMENTS

| | | | |
|---|---|---|---|
| 4,607,228 A | 8/1986 | Reif | |
| 4,644,806 A * | 2/1987 | Flagg et al. | 73/863.58 |
| 4,888,948 A * | 12/1989 | Fisher et al. | 60/223 |
| 5,070,722 A * | 12/1991 | Hawman et al. | 73/28.01 |
| 5,357,197 A * | 10/1994 | Sorkin | 324/204 |
| 5,571,946 A | 11/1996 | Koshi et al. | |
| 5,705,930 A * | 1/1998 | Forfitt | 324/453 |
| 5,760,298 A * | 6/1998 | Fisher et al. | 73/61.42 |
| 5,811,664 A * | 9/1998 | Whittington et al. | 73/53.07 |
| 6,489,775 B1 | 12/2002 | Rigby et al. | |
| 7,837,149 B2 * | 11/2010 | Mackin | 244/134 F |
| 8,204,671 B2 * | 6/2012 | Agrawal et al. | 701/100 |
| 8,256,277 B2 * | 9/2012 | Khibnik et al. | 73/112.01 |
| 8,459,103 B2 * | 6/2013 | Khibnik et al. | 73/112.01 |
| 2009/0031801 A1 * | 2/2009 | Martindale et al. | 73/431 |
| 2009/0112519 A1 * | 4/2009 | Novis et al. | 702/183 |
| 2010/0187907 A1 * | 7/2010 | Toba et al. | 307/48 |
| 2010/0287907 A1 * | 11/2010 | Agrawal et al. | 60/39.091 |
| 2010/0313639 A1 | 12/2010 | Khibnik et al. | |
| 2011/0010071 A1 | 1/2011 | Rhodes et al. | |
| 2011/0179763 A1 * | 7/2011 | Rajamani et al. | 60/39.092 |

OTHER PUBLICATIONS

U.S. Appl. No. 13/168,293, "IDMS Signal Processing to Distinguish Inlet Particulates," filed Jun. 24, 2011.

* cited by examiner

*Primary Examiner* — Peter Macchiarolo
*Assistant Examiner* — Mohammed Keramet-Amircola
(74) *Attorney, Agent, or Firm* — Carlson, Gaskey & Olds, P.C.

(57) ABSTRACT

An example aircraft debris monitoring sensor assembly includes an aircraft conduit defining a hollow core passage extending axially from an inlet opening to an outlet opening. A sensor arrangement detects debris carried by a fluid within the hollow core passage.

23 Claims, 6 Drawing Sheets

US 9,010,198 B2

AIRCRAFT DEBRIS MONITORING SENSOR ASSEMBLY

BACKGROUND

This disclosure relates generally to monitoring debris and, more particularly, to detecting debris using debris sensors mounted outside an aircraft engine.

Aircraft operate in various environments. Some environments include debris, such as volcanic ash, dust, and sand. Debris can undesirably accelerate wear and erosion of the aircraft components.

Some aircraft engines utilize inlet debris monitoring systems to detect and monitor particles of debris carried by air in the aircraft engine. These systems typically include one or more debris sensors located within the aircraft engine. The debris sensors may detect debris by sensing the electrostatic charge of debris. The system then compiles the detection information for monitoring purposes.

The aircraft engine is a relatively large structure that can influence air movement. That is, movement of air into the aircraft engine is not the same as the movement of air areas in areas outside of the aircraft engine. The aircraft engine's influence may change the quantity of debris carried air, and even the makeup of debris carried by this air, relative to areas outside the aircraft engine. Thus, debris measurements from sensors within the aircraft engine may not accurately reflect debris in areas outside the aircraft engine and the makeup of debris in areas outside the aircraft engine.

SUMMARY

An example aircraft debris monitoring sensor assembly includes an aircraft conduit defining a hollow core passage extending axially from an inlet opening to an outlet opening. A sensor arrangement detects debris carried by a fluid within the hollow core passage.

An example aircraft debris monitoring sensor assembly includes an aircraft conduit extending axially from an inlet opening to an outlet opening and a sensor arrangement that detects debris carried by fluid moving through the conduit. A gas turbine engine moves the aircraft conduit to move air through a flow passage of the aircraft conduit. The flow passage extends from the inlet opening to the outlet opening. The flow passage is separate and distinct from any flow passage of the gas turbine engine.

An example method of analyzing debris includes analyzing debris carried by a fluid using an electrostatic charge carried by the debris. The fluid is within a hollow conduit passage that extends between an inlet and an outlet of an aircraft conduit. The method moves the aircraft conduit to move the fluid relative to the aircraft conduit between the conduit inlet and the conduit outlet.

These and other features of the example disclosure can be best understood from the following specification and drawings, the following of which is a brief description.

DETAILED DESCRIPTION

Figure 1:
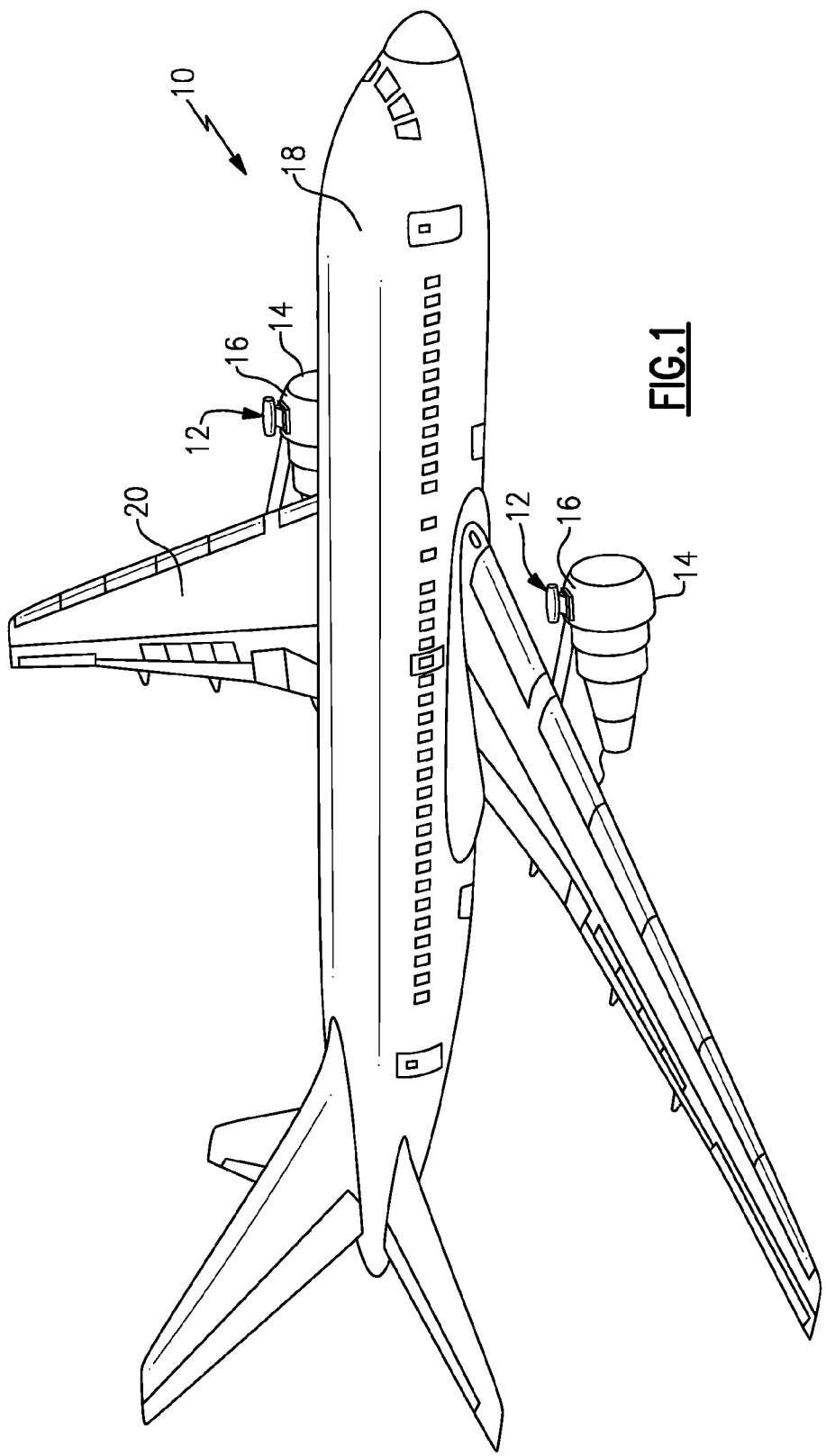
FIG. 1 shows an aircraft having an example debris monitoring assembly.
Figure 2:
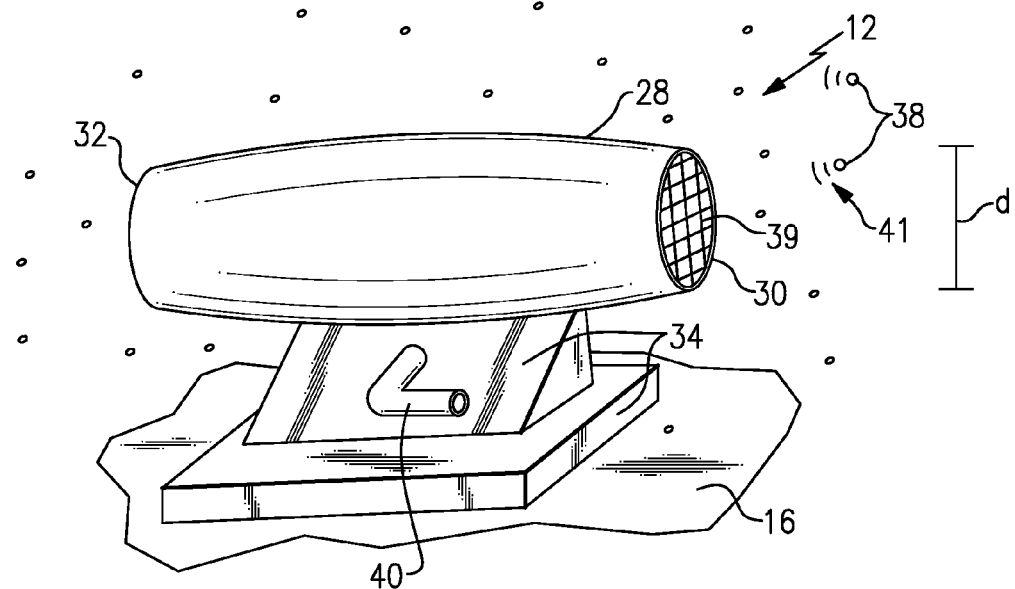
FIG. 2 shows a perspective view of the FIG. 1 debris monitoring assembly.
Figure 3:
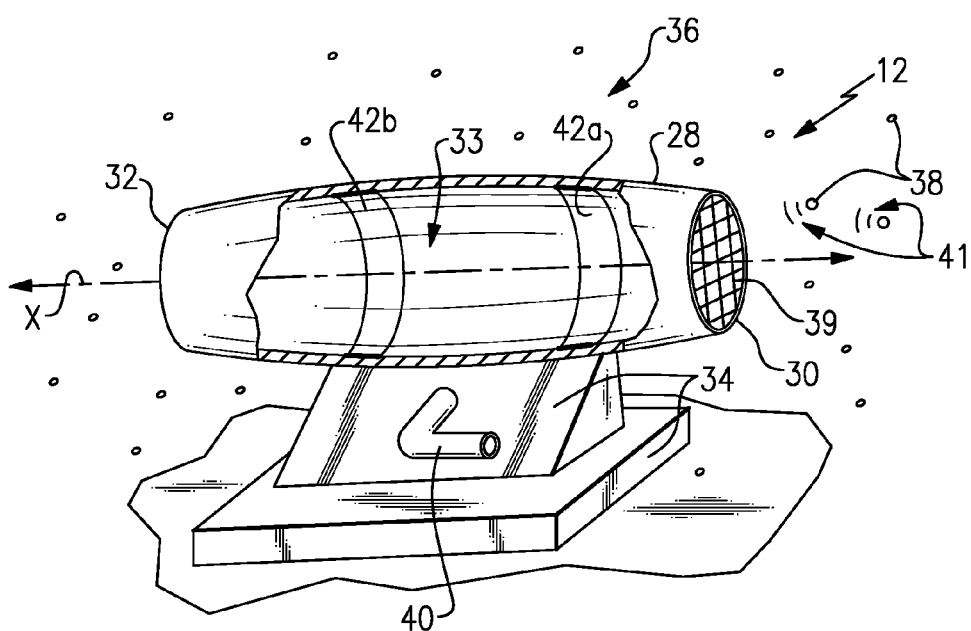
FIG. 3 shows a partial section view of the FIG. 2 debris monitoring assembly.

Referring to FIGS. 1-3, an example aircraft 10 includes at least one debris monitoring sensor assembly 12 and at least one aircraft engine 14. The aircraft 10 is a helicopter in another example.

In this example, the debris monitoring sensor assembly 12 is mounted directly to an outwardly facing surface 16 of the engine 14 behind an inlet to the engine 14 (relative to a nose of the aircraft 10). The debris monitoring sensor assembly 12 is thus outside the engine 14. In other examples, the debris monitoring sensor assembly 12 is mounted to a fuselage 18, a wing 20, or to some other area of the aircraft 10 that is also outside the engine 14.

The example debris monitoring sensor assembly 12 includes a conduit 28 or another type of aircraft housing. The conduit 28 extends along an axis X from an inlet opening 30 to an outlet opening 32. The conduit 28 defines a hollow core passage 33, which, in this example, has a nonannular (and circular) cross-sectional area. The hollow core passage 33 is uninterrupted along its entire axial length. The example conduit 28 is considered a nonmechanical conduit as the conduit 28 houses no mechanical components.

The conduit 28 is secured to a support structure 34, which is attached directly to the outwardly facing surface 16 of the engine 14. The support 34 spaces the conduit 28 from the outwardly facing surface 16 allowing the cylindrical conduit 28 to stick out into the jet stream relative to the engine 14.

The engine 14 propels the aircraft 10. As can be appreciated, fluid (e.g., air) communicates through the conduit 28 of the debris monitoring assembly 12 when the aircraft 10 is propelled by the engine 14. Fluid enters the conduit 28 at the inlet opening 30, moves along the hollow core passage 33, and exits the conduit 28 at the outlet opening 32. Fluid moves from the outlet opening 32 directly to atmosphere.

Notably, there are no components, and certainly no compressor components, housed by the conduit 28. Thus, the pressure of the fluid does not substantially change as the fluid moves through the conduit 28. The temperature of the fluid also remains the same throughout the conduit 28. Because the conduit 28 is outside the engine 14, the hollow core passage 33 is considered a flow path that is separate from any flow path of the engine 14.

In this example, a sensor arrangement 36 within the debris monitoring sensor assembly 12 is used to analyze debris 38 carried by the fluid within the conduit 28. Example types of debris 38 include volcanic ash, which are typically considered tephra fragments smaller than 0.08 inches (2 millimeters) in diameter, and may include very fine particulate much smaller than 0.08 inches (2 millimeters). After a volcanic eruption, volcanic ash can remain airborne for several days or even weeks. Aircraft components can become damaged or worn due to flights through volcanic ash. If the damage or wear to the engine 14 is significant, the engine 14 may seize and shut down. Other types of debris 38 may include dust, sand, etc.

Analyzing the debris 38 by, for example, quantifying the debris 38, identifying the debris 38, etc. is useful. Debris of different sizes can differently affect each component. For this reason, it is helpful to distinguish between particulate flow rates for different particulate sizes or size ranges of the debris 38. Similarly, particulates of different materials may cause more or less damage, wear, or performance loss of different kinds. Fine particulates (such as the volcanic ash), may pose a greater risk of clogging, while large, hard particulates may cause increased erosion.

A filter 39 covers the first inlet opening 30 to prevent relatively large debris, such as large rocks or chunks of ice, from entering the conduit 28. The example filter 39 is screwed directly to the conduit 28. The filter 39 is a metallic screen, for example.

A pitot tube 40 may be integrated with the debris monitoring assembly 12. The pitot tube 40 measures the relative velocity of fluid moving through the conduit 28 of the debris monitoring assembly 12, which may improve the accuracy of debris measurements involving quantifying and identifying the debris 38. In this example, the pitot tube 40 and the conduit 28 are both supported by the support 34.

The example sensor arrangement 36 measures electrostatic charges 41 carried by the debris 38 moving through the conduit 28. The debris 38 become charged due to, for example, interactions between different particles of the debris 38. For clarity, this example only shows some of the debris 38 having the electrostatic charges 41. However, nearly all of the debris 38 provide some electrostatic charge that is detectable the sensor arrangement 36. The electrostatic charges 41 are detected due to a potential difference between a sensor 42a of the sensor arrangement 36 and the conduit 28 (which is grounded). The sensor arrangement 36 also includes a second sensor 42a used to detect the debris 38.

The electrostatic charges 41 from the debris 38 induce a time-domain signal current when passing through the sensor arrangement 36. The signal is communicated away from the sensor arrangement 36 as a signal that fluctuates with changes in the electromagnetic field through the plain of the sensors within the sensor arrangement 36.

The example sensor arrangement 36 includes the first sensor 42a and the second sensor 42b. Although a single sensor may be used, using more than one sensor within the sensor arrangement 36 may improve sensitivity to debris 38, help validate signatures of the debris 38, help track the debris 38, help measure parameters of the debris 38, etc. More than two sensors 42a and 42b could also be used.

In this example, the first sensor 42a and the second sensor 42b are both rings. In other examples, the first sensor 42a (and/or the second sensor 42b) is a group of several individual sensors that are axially aligned and distributed circumferentially about the axis X, or a single button sensor or a single arc sensor, etc. The first sensor 42a and the second sensor 42b are typically made of a conducting material, such as copper or aluminum.

The first sensor 42a and the second sensor 42b may be epoxied over to provide a relatively smooth surface facing flow through the conduit 28 together with the inner walls of the conduit. The epoxy does not substantially affect the debris detection by the first sensor 42a and the second sensor 42b while improving life of the first sensor 42a and the second sensor 42b.

In this example, the first sensor 42a is axially narrower than the second sensor 42b and has less surface area available for monitoring the debris 38. The first sensor 42a is thus less sensitive to electrostatic charges 41 from the debris 38 than the second sensor 42b, but provides a higher signal-to-noise ratio of electrostatic charges 41 that are detected. In other examples, relative differences between the radial diameters of the sensors 42a and 42b result in varied sensitivity to electrostatic charges 41. Still other examples variables include changing the material of the sensors 42a and 42b, their orientation within the conduit 28, designing gaps or other variations within the sensors 42a and 42b, or altering how the sensors 42a and 42b are mounted (attached using glue, with insulating materials, etc.)

The example debris monitoring sensor assembly 12 has a diameter d that is between 1 inches (25.4 millimeter) and 10 inches (254 millimeters). As can be appreciated, this diameter is smaller than a diameter of the gas turbine engine 14.

Figure 4:
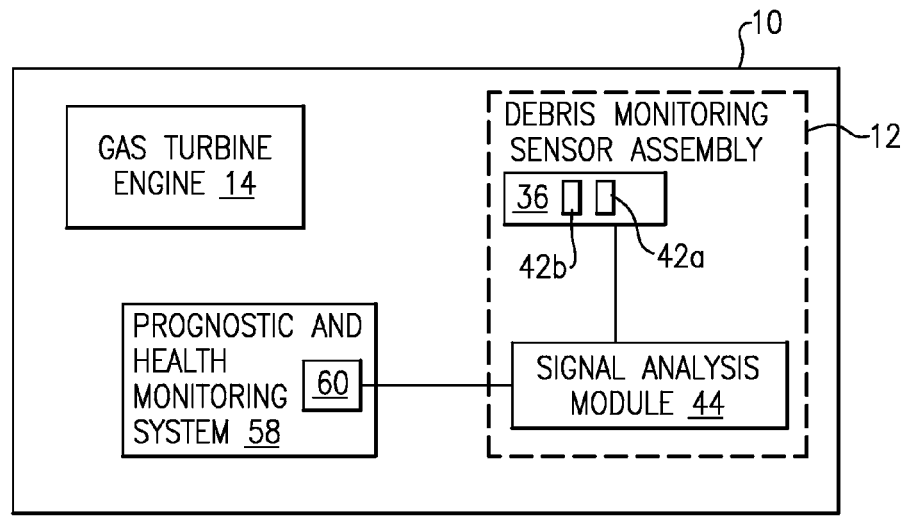
FIG. 4 shows schematic view of the FIG. 1 aircraft.
Figure 5:
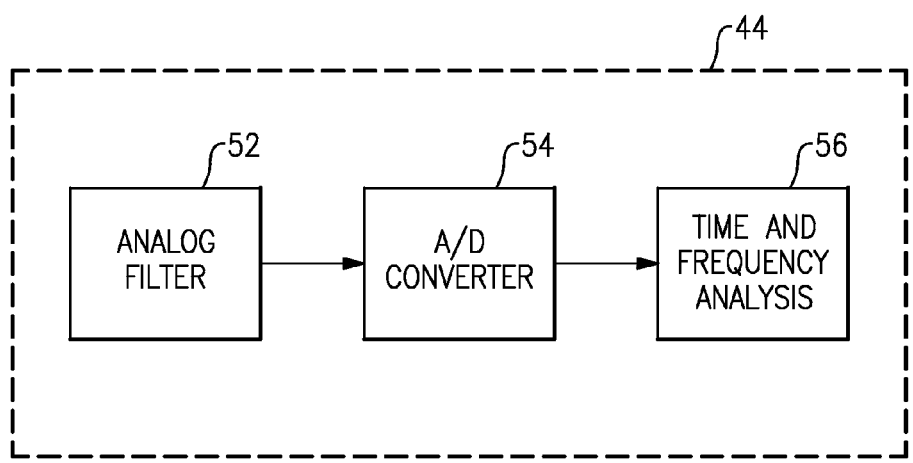
FIG. 5 shows a schematic view of the signal analysis module of FIG. 4.
Figure 6:
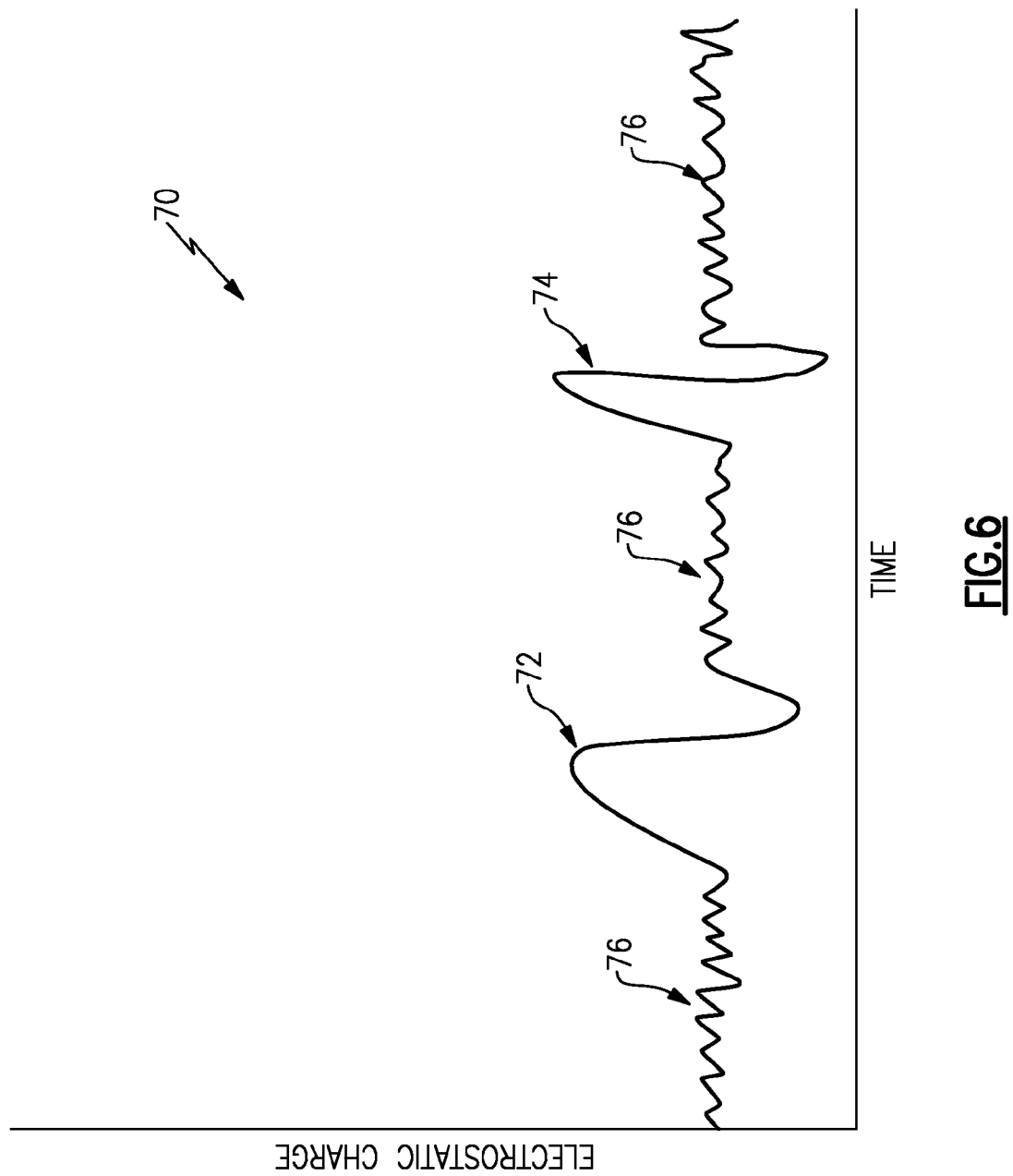
FIG. 6 shows an example graphical output from the FIG. 1 debris monitoring assembly.

Referring now to FIGS. 4-6 with continuing reference to FIG. 3, a signal analysis module 44 processes the signal from the sensor arrangement 36 and may also use information from the pitot tube 40. The signal from the signal analysis module 44 is shown graphically as an electrostatic charge graph 70. A first pulse 72 represents an electrostatic charge from one particle of the debris 38 moving axially past the sensor 42a. A second pulse 74 represents the electrostatic charge from another particle of the debris 38 moving axially past the sensor 42a. Generally, the pulses 72 and 74 are the portions of the electrostatic charge graph 70 extending beyond noise portions 76 of the electrostatic charge graph 70. In one example, the signal analysis module 44 increases the signal-to-noise ratio for the electrostatic charge graph 70, to clarify differences between the pulses 72 and 74, and the noise portions 76. A prognostic and health monitoring system 58 may receive the signal and estimate the size and quantity of the particles based on the amplitude and width of respective pulses 72 and 74, for example.

A controller module 60 of the example prognostic and health monitoring system 58 is configured to selectively initiate detecting the debris 38 using the first sensor 42a, the second sensor 42b, or both. The example controller module 60 initiates a particular combination of sensors within the sensor arrangement 36 to desirably achieve relatively high signal-to-noise ratios between the pulses 72 and 74 and the noise portions 76 of the electrostatic charge graph 70.

The controller module 60 may initiate a particular combination of sensors within the sensor arrangement 36 to achieve a higher sensitivity to electrostatic charges 41. For example, if the debris 38 entering the conduit 28 have relatively low electrostatic charges, the controller module 60 initiates detection of the debris 38 using only the second sensor 42b, which is more sensitive to electrostatic charge than the first sensor 42a. By contrast, if the debris 38 entering conduit 28 have a relatively high electrostatic charges, the controller module 60 initiates detection of the debris 38 using only the first sensor 42a, which is less sensitive to electrostatic charges 41 than the second sensor 42b. In some examples, the controller module 60 initiates detection of the debris 38 using both the first sensor 42a and the second sensor 42b.

As known, the size of the electrostatic charge 41 from particles of the debris 38 are related to the size and type of the debris 38 and also to the mixture of debris 38 of different sizes. Examples of the debris 38 having a relatively low electrostatic charge include isolated bits of fine sand or bugs. Examples of the debris 38 having relatively high electrostatic charge include a cloud of fine particles of volcanic ash or fine sand.

Measured charge is a function of the surface area of the sensors 42a and 42b, the debris 38 distance from the sensors 42a and 42b and exposure time (which is a function of the velocity of the debris). Sequentially monitoring some types of debris 38 is often appropriate because the debris 38 are relatively consistent as they move through the conduit 28, a sandstorm for example. Thus, sequential monitoring will not result in loss of information.

In one example, the speed of the debris 38 moving through the conduit 28 is determined by measuring electrostatic charges 41 of debris 38 using the first sensor 42a and then switching to measure electrostatic charges 41 from the same debris 38 (or cloud of debris) using the second sensor 42b.

Alternatively, if both the first sensor 42a and the second sensor 42b are simultaneously detecting debris 38, an interval between the respective pulses from the sensors 42a and 42b can indicate the speed of the debris 38. A person skilled in the art and having the benefit of this disclosure would be able to determine the speed of the debris 38 moving through the conduit 28.

The example signal analysis module 44 includes an analog filter 52, an analog/digital convertor 54, and time-and-frequency analysis module 56. The signal analysis module 44 is housed within the support 34 in this example. In another example, wireless communications are used to communicate information from the first sensor 42a and the second sensor 42b to another area of the aircraft 10 or a ground-based system.

Processing at the signal analysis module 44 may include digitizing and adjusting the signal using the analog filter 52 and the analog/digital convertor 54. Other examples of processing include amplifying the signal, calibrating the signal, and correlating the signal.

In one example, the time-and-frequency analysis module 56 Fourier transforms this time-domain signal from the analog/digital convertor 54 to produce a frequency-domain signal. Time-and-frequency analysis module 56 then divides this frequency-domain signal into a plurality of bins. These bins may, for instance, be frequency ranges of the frequency-domain sensor signal. Such bins can cover regular, overlapping or non-overlapping ranges, or can cover dynamically updated frequency ranges specified by signal analysis module 44 in response to characteristics of the digitized frequency-domain sensor signal. Each bin corresponds to a particle composition range, with higher frequencies generally corresponding to smaller particulates, and lower frequencies corresponding to larger particulates.

The frequency-domain signal, the bin information, or both is communicated to the prognostic and health monitoring system 58, which then may indicate the presence of the debris 38 (or otherwise characterize the debris 38) in the form of an alert, for example. This debris characterization may also be stored in a log for retrieval during maintenance of components of the aircraft 10, forwarded to an aircraft cockpit, or both. The controller module 60 may initiate the alert or store the debris characterization.

Once alerted, a pilot, maintenance worker, etc. can then take appropriate actions in response to the alert. The pilot may choose to avoid or maneuver the aircraft 10 out of areas having particularly damaging quantities of debris or particularly damaging types of debris. The alert is a light (or another visual indicator) or an audible alert, for example.

Figure 7:
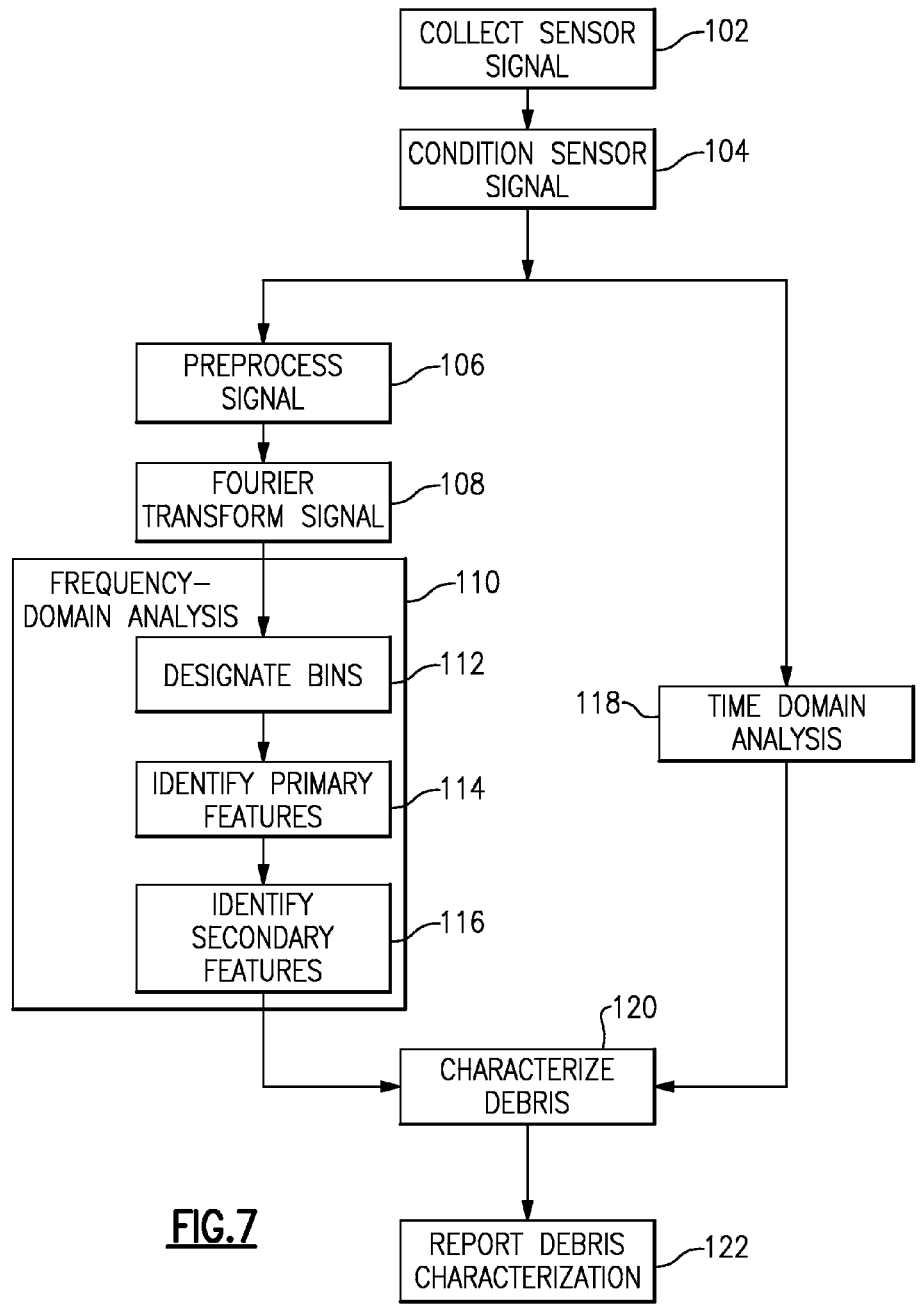
FIG. 7 shows the flow of a debris monitoring method associated with the FIG. 2 debris monitoring assembly.

Referring to FIG. 7 with continuing reference to FIGS. 4-5, an example method 100 using the debris monitoring assembly 12 includes monitoring debris using debris sensors 42a and 42b to collect at least one sensor signal at a step 102. The signal analysis module 44 conditions the signal and translates the result into a digital signal at a step 104.

At a step 106, a signal preprocessor (not shown) may apply additional filter functions dependent on the features to be extracted from the sensor signal by signal analysis module 44, as described above. Signal analysis module 44 Fourier transforms the digitized sensor signal at a step 108, and analyzes the resulting frequency-domain sensor signal to produce the debris characterization at a step 110.

As a first step of this analysis, the frequency domain sensor signal is subdivided into a plurality of frequency range bins, which may be of fixed or variable width at a step 112. Within each bin, signal analysis module 44 extracts a plurality of primary features, including signal amplitude, signal power, and signal power spectrum slope at a step 114. Signal analysis module 44 next produces a series of secondary features, which reflect second-order properties derived from the primary features, such as energy ratios or rates or change at a step 116. Secondary features may, for instance, include ratios of power or rates of change of primary features in different bins, or relationships between different primary features, such as amplitude and power.

In this example, signal analysis module 44 also analyzes time-domain sensor signals, as known in the prior art, at a step 118. For example, signal analysis module 44 receives time domain-signals from the sensors 42a and 42b, and processes these signals to produce time-domain signal features such as the times and amplitudes of peaks corresponding to discrete debris ingestion events.

The debris are characterized according to the primary and secondary features of the frequency-domain signal at a step 116, and reported as a debris characterization at a step 122. The step 120 may use the time-domain signal features form the step 118.

Figure 8:
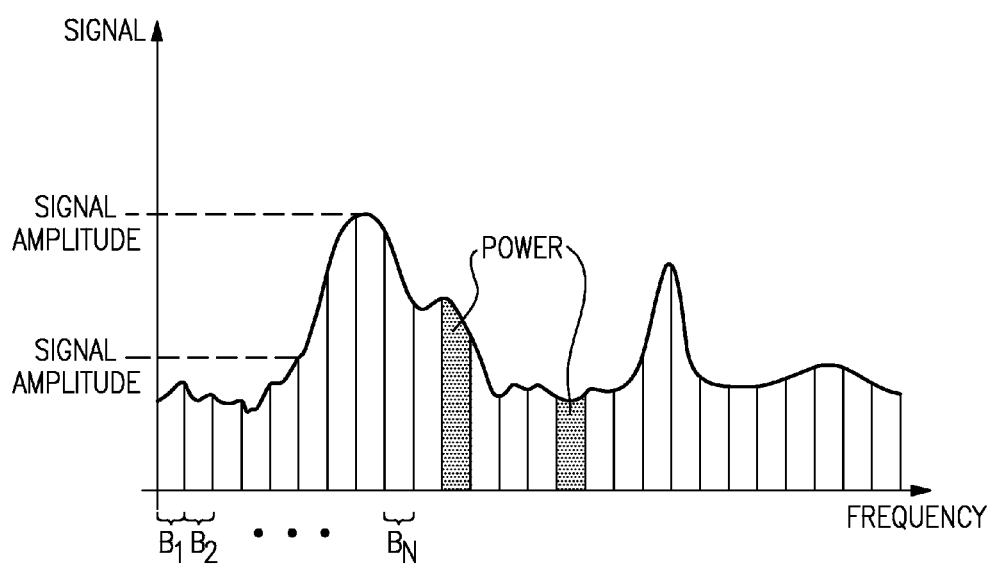
FIG. 8 is a graph of an example sensor signal as a function of frequency, and indicating signal features monitored by the method of FIG. 7.

FIG. 8 is a graph of an example sensor frequency-domain sensor signal. FIG. 8 shows a plurality of bins B1 through BN designated by the signal analysis module 44 (FIGS. 4-5). These bins are depicted as having regular widths covering a short frequency range, but may alternatively span irregular frequency ranges. Each bin corresponds to a range of particulate composition, such as range of particulate diameter or mass.

A variety of primary features may be assigned to each bin, such as signal amplitude or power, as shown. These features may comprise mean or median values within the bin, such as mean amplitude or median power spectrum slope. Each primary feature provides an indication of mass flow rate of particulates of a composition corresponding to the frequency range of the bin.

Features of the disclosed examples include monitoring of debris using sensors outside an aircraft engine. The assemblies holding the sensors are robust as there are no mechanical or exposed electrical parts.

The sensors may be controlled to detect certain types of debris. Also, by analyzing debris sensor signals in the frequency domain, some of the disclosed examples characterize the composition of particulate debris. This characterization allows for more precise maintenance scheduling, reducing maintenance costs and improving aircraft safety.

In some examples, generic measurements about debris are fed from the debris monitoring assembly to the pilot, who then makes adjustments to the operation of the engine (or other areas of the aircraft) based on the measurements. The pilot may also initiate adjustments to physical components associated with the engine (or other areas of the aircraft). The information may include estimates to how much loss of lift is associated with a particular amount or type of debris.

The information may also be sent to other aircraft within a fleet of the aircraft. The information may help define a cloud of volcanic ash (or another type of debris). The aircraft within the fleet may adjust flight patterns based on the cloud of volcanic ash. Over time, cumulative information may be used to predict wear and erosion on components of the engine or other components of the aircraft, such as lift producing components of the aircraft.

Although a preferred embodiment has been disclosed, a worker of ordinary skill in this art would recognize that certain modifications, such as adding additional sensors, would come within the scope of this invention. For that reason, the following claims should be studied to determine the true scope and content of this invention.

We claim:

1. An aircraft debris monitoring sensor assembly, comprising:
    an aircraft conduit defining a hollow core passage extending axially from an inlet opening to an outlet opening;
    a sensor arrangement that detects debris carried by a fluid within the hollow core passage; and
    a pitot tube secured relative to the aircraft conduit, the pitot tube is configured to receive a first flow of air and the aircraft conduit is configured to receive a second flow of air that is different than the first flow of air.

2. The debris monitoring sensor assembly of claim 1, wherein the pitot tube and aircraft conduit are positioned relative an aircraft using a common support.

3. An aircraft debris monitoring sensor assembly, comprising:
    an aircraft conduit defining a hollow core passage extending axially from an inlet opening to an outlet opening;
    a sensor arrangement that detects debris carried by a fluid within the hollow core passage, the sensor arrangement comprising a first ring sensor and a second ring sensor; and
    a controller configured to selectively initiate debris detection using the first ring sensor or the second ring sensor.

4. The aircraft debris monitoring system of claim 3, wherein the hollow core passage is uninterrupted across its entire diameter from the inlet opening to the outlet opening.

5. The aircraft debris monitoring system of claim 3, wherein a pressure of a fluid within the hollow core passage is substantially the same along the entire axial length of the hollow core passage.

6. The aircraft debris monitoring sensor assembly of claim 3, wherein the aircraft conduit is a nonmechanical aircraft conduit.

7. The aircraft debris monitoring sensor assembly of claim 3, wherein the hollow core passage is nonannular.

8. The aircraft debris monitoring sensor assembly of claim 3, including a filter covering the inlet opening.

9. The aircraft debris monitoring sensor assembly of claim 3, including a support that spaces the conduit from an outwardly facing surface of an aircraft.

10. The aircraft debris monitoring sensor assembly of claim 3, wherein fluid exiting the aircraft conduit from the outlet opening is communicated directly to atmosphere.

11. The aircraft debris monitoring sensor assembly of claim 3, wherein the fluid is a jet stream fluid.

12. The aircraft debris monitoring sensor assembly of claim 3, wherein the hollow core passage is open and uninterrupted across an entire diameter of the aircraft conduit.

13. The aircraft debris monitoring sensor assembly of claim 3, further comprising:
    a gas turbine engine that moves the aircraft conduit to move air through a flow passage of the aircraft conduit extending from the inlet opening to the outlet opening, wherein the flow passage is separate and distinct from any flow passage of the gas turbine engine.

14. The aircraft debris monitoring sensor assembly of claim 13, wherein the aircraft conduit defines a uninterrupted and hollow core passage extending from the inlet opening to the outlet opening, the inlet opening provided by a forwardmost edge of the aircraft conduit, the outlet opening provided by a rearwardmost edge of the aircraft conduit.

15. The aircraft debris monitoring sensor assembly of claim 13, including a support that secures the aircraft conduit to an outwardly facing surface of the gas turbine engine.

16. A method of analyzing debris comprising:
    analyzing debris carried by a fluid using an electrostatic charge of the debris, the fluid within a hollow conduit passage that extends between an inlet and an outlet of an aircraft conduit;
    moving the aircraft conduit to move the fluid relative to the aircraft conduit between the conduit inlet and the conduit outlet; and
    using a sensor arrangement to determine the electrostatic charge, the sensor arrangement comprising at least one sensor distributed circumferentially about an axis of the sensor housing.

17. The method of claim 16, wherein the analyzing comprises detecting debris by measuring an electrostatic charge of the debris.

18. The method of claim 16, including alternating between a first debris sensor of the sensor arrangement and a second debris sensor of the sensor arrangement in response to a type of debris.

19. The method of claim 16, estimating a loss of lift using information about the debris collected during the analyzing.

20. The aircraft debris monitoring sensor assembly of claim 3, wherein the hollow core passage has a diameter and the hollow core passage extends continuously across the entire diameter from a first radially inner wall of the aircraft conduit wall to an opposing, second radially inner wall of the aircraft conduit.

21. The method of claim 16, wherein the hollow conduit passage extends radially and continuously between opposing radially inwardly facing walls of an aircraft conduit.

22. The method of claim 16, wherein the inlet is provided by a forwardmost edge of the aircraft conduit, and the outlet is provided by a rearwardmost edge of the aircraft conduit.

23. The aircraft debris monitoring sensor assembly of claim 1, wherein the pitot tube is configured to recieve a first flow of air and the hollow conduit is configured to receive a second flow of air that is different than the first flow of air.

* * * * *